United States Patent [19]

Fertig et al.

[11] Patent Number: 4,598,201

[45] Date of Patent: Jul. 1, 1986

[54] INFRARED FLUID ANALYZER EMPLOYING A PNEUMATIC DETECTOR

[75] Inventors: Glenn H. Fertig, Natrona Heights; Robert J. Wozniak, Belle Vernon, both of Pa.

[73] Assignee: Mine Safety Appliances Company, Pittsburgh, Pa.

[21] Appl. No.: 638,995

[22] Filed: Aug. 9, 1984

[51] Int. Cl.$^4$ .................................................. G01N 21/37
[52] U.S. Cl. .................................. 250/343; 250/252.1; 250/352; 250/493.1
[58] Field of Search ............ 250/343, 352, 351, 252.1, 250/493.1, 344, 345, 346; 374/168, 184

[56] References Cited

U.S. PATENT DOCUMENTS

| | | | |
|---|---|---|---|
| 2,681,415 | 6/1954 | Liston | 250/345 |
| 3,212,211 | 10/1965 | Bennett | 239/706 |
| 3,854,050 | 12/1974 | Peterson et al. | 250/429 |
| 3,968,369 | 7/1976 | Luft | 250/344 |
| 3,970,387 | 7/1976 | Faulhaber et al. | 356/51 |
| 4,004,146 | 1/1977 | Blunck | 250/345 |
| 4,103,174 | 7/1978 | McClatchie et al. | 250/493.1 |
| 4,134,447 | 1/1979 | Jennings et al. | 165/30 |

FOREIGN PATENT DOCUMENTS 2229356 9/1973 Fed. Rep. of Germany ...... 250/343
732700 6/1955 United Kingdom .

OTHER PUBLICATIONS

V. H. Allen and J. G. Bayly, "On-Line Heavy-Water Monitors Based on the Absorption of Infrared Energy", *IEEE Transactions on Nuclear Science*, vol. NS-23, No. 1 (Feb. 1976) pp. 317–320.

P. D. Goldan and K. Goto, "An Acoustically Resonant System for Detection of Low-Level Infrared Absorption in Atmospheric Pollutants", *Journal of Applied Physics*, vol. 45, No. 10 (Oct. 1974) pp. 4350–4355.

W. G. Fastie and A. H. Pfund, "Selective Infra-Red Gas Analyzers", *Journal of the Optical Society of America*, vol 37, No. 10 (Oct. 1947) pp. 762–768.

M. C. Killion and E. V. Carlson, "A Subminiature Electret-Condenser Microphone of New Design", *Journal of the Audio Engineering Society*, vol. 22, No. 4 (May 1974) pp. 237–243.

Primary Examiner—Craig E. Church
Assistant Examiner—Constantine Hannaher
Attorney, Agent, or Firm—Reed, Smith, Shaw & McClay

[57] ABSTRACT

An infrared fluid analyzer with an improved sensitivity and signal to noise ratio is provided. The device includes a capacitor microphone for detecting absorption by the sample of characteristic infrared wavelength lines, and utilizes an electret material to electrically polarize the capacitive element. Also included are means for controlling the temperature of the infrared radiation source in order to stabilize the output thereof and increase the reliability of the instrument, and means for controlling the temperature of the fluid sample. In a double-beam embodiment of the invention, a gas-free reference cell is provided to further stabilize the instrument.

16 Claims, 9 Drawing Figures

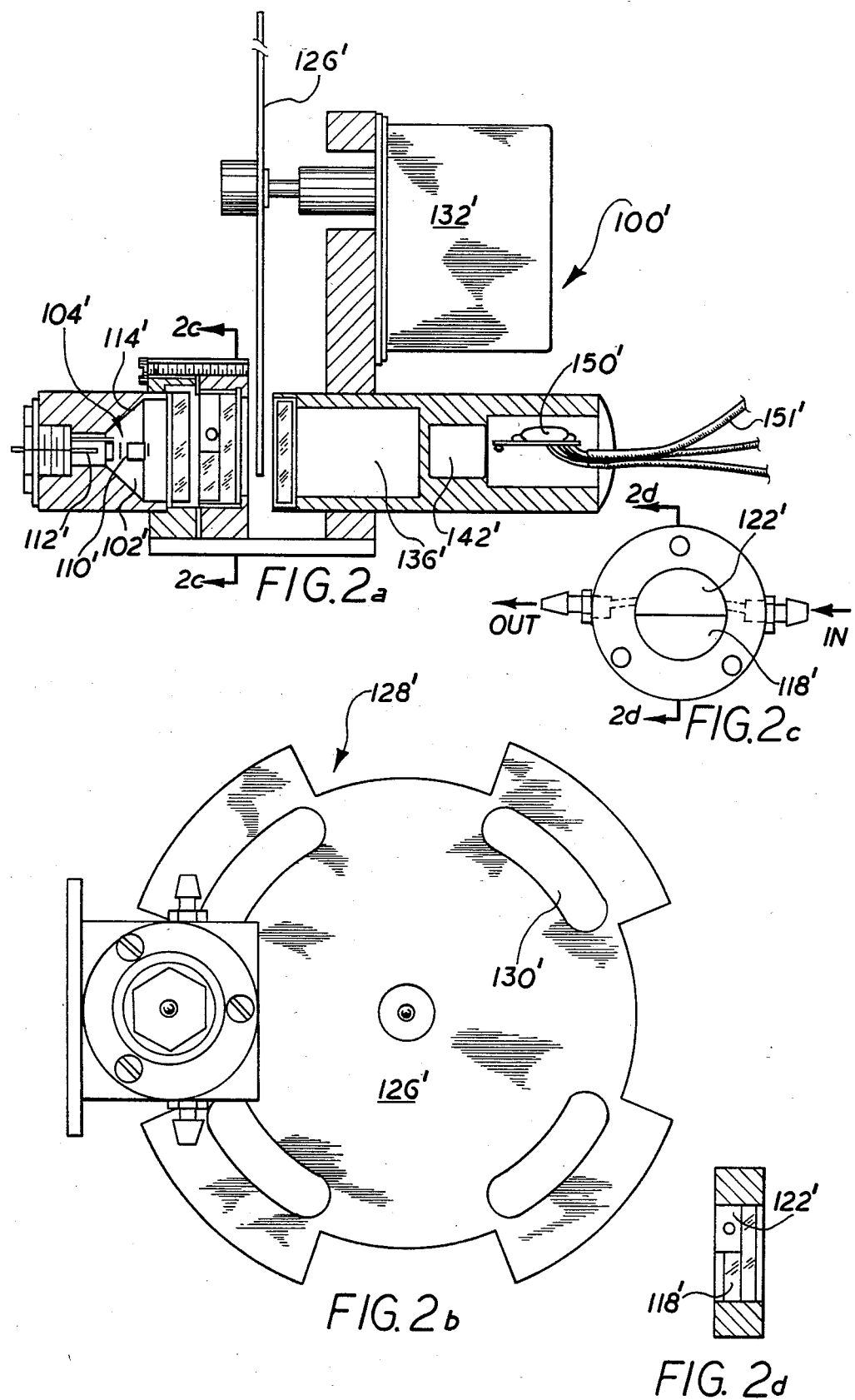

INFRARED FLUID ANALYZER EMPLOYING A PNEUMATIC DETECTOR

FIELD OF THE INVENTION

The invention relates to devices for analyzing a fluid using infrared absorption techniques, and in particular to such devices using pneumatic detectors.

DISCUSSION OF THE TECHNICAL PROBLEM

Many types of devices for analyzing a fluid using infrared absorption techniques are known in the art, e.g., U.S. Pat. No. 4,004,146. Commonly such devices include a source of infrared radiation, reference and sample cells through which the infrared radiation is alternately passed and a pneumatic detector device which responds to the difference between the energy of the incident beams from reference and sample cells within the spectral range of the gas in question, e.g. U.S. Pat. Nos. 2,681,415; 3,968,369; and 3,970,387. As disclosed in U.S. Pat. No. 3,212,211, the energy difference causes pressure changes in the gas within the pneumatic detector which when detected and amplified yield information concerning the composition of the fluid in the sample cell.

A "LUFT" type pneumatic detector is well known in the art and includes a capacitor microphone system for detecting pressure changes within the gas chamber of the pneumatic detector. The capacitor microphone is typically constructed of a thin moveable diaphragm of gold or aluminum foil which forms the first plate of the capacitor, and a second spaced-apart plate serving as the stator of the capacitor. The diaphragm is in communication with the gas chamber and moves in response to pressure changes therein. The capacitor is electrically polarized by a resistor and source of EMF in series between the diaphragm and stator, such that movement of the diaphragm results in a signal corresponding to the change in capacitance. This signal is then amplified and displayed on a meter.

While such a device has proved useful for some time, it is limited in its sensitivity because of electrical noise which exists in the system due to the existence of the resistor and EMF source which polarizes the capacitor microphone. As the resistance in the system increases, the noise in the system also increases. Likewise, as the temperature of the resistor increases, noise increases. Accordingly, the problem is particularly troublesome because the noise level (and therefore the sensitivity of the pneumatic detector) changes with temperature. It would be desirable to have a pneumatic detector for use in an infrared analyzer which minimized the noise in the system, and which does not vary in sensitivity with changes of temperature.

Conventional infrared analyzers are also rendered less reliable because of their use of a reference cell which is hermetically sealed and contains a selected reference gas. Inherent in such a system is the likelihood that the seal of the reference cell will be imperfect or will be damaged in use and the "reference gas" will be of a changing composition. In this event the accuracy of the infrared analyzer would be compromised. It would be desirable to have a double beam infrared analyzer in which the reference cell was more certain to remain constant with respect to the infrared radiation passing therethrough.

Finally, it has been determined that conventional infrared analyzers may be limited by a lack of temperature control of both the infrared radiation source and the sample fluid which is to be analyzed. It has been determined that common infrared radiation sources vary their output in relation to their temperature, such that many hours may elapse from the time of initial activation to the time when a steady-state output is achieved. This instability is of particular concern in "single beam" infrared analyzer in which a reference cell is not utilized. In addition, condensation of the sample fluid is a problem in conventional infrared analyzers which could be minimized by proper temperature control facilities.

It would be desirable to have an infrared analyzer which was not subject to temperature-related instabilities and which accordingly would yield reliable results shortly after activation. It would be likewise desirable to have an infrared analyzer with facilities for assuring that the sample fluid would not tend to condense in the sample cell.

SUMMARY OF THE INVENTION

The present invention provides an improved infrared fluid analyzer which includes a pneumatic detector which substantially improves the signal to noise ratio and sensitivity of the system by polarizing the capacitive element thereof through the use of electret materials. In this manner the prior art resistor and source of EMF may be eliminated, thereby simplifying the detector circuitry while reducing noise levels and eliminating the temperature dependence of the system to improve stability.

The present invention also provides improved stability to the infrared analyzer by including a novel temperature control system which maintains the temperature of the infrared radiation source and the sample cell at a preselected steady state operating temperature and thereby minimizes variations in the infrared radiation source output levels and undesirable condensation in the sample cell.

Further, the present invention provides a novel, solid material reference cell construction in the double beam form of the analyzer. Through this advancement, the reference cell is maintained as an optical constant, as opposed to previous gas-filled reference cell which were prone to leakage and corresponding change in optical characteristic.

DESCRIPTION OF THE DRAWINGS

FIG. 2a–d is a presently preferred embodiment of the analyzer schematically shown in FIG. 2;

DESCRIPTION OF PREFERRED EMBODIMENTS

Figure 1:
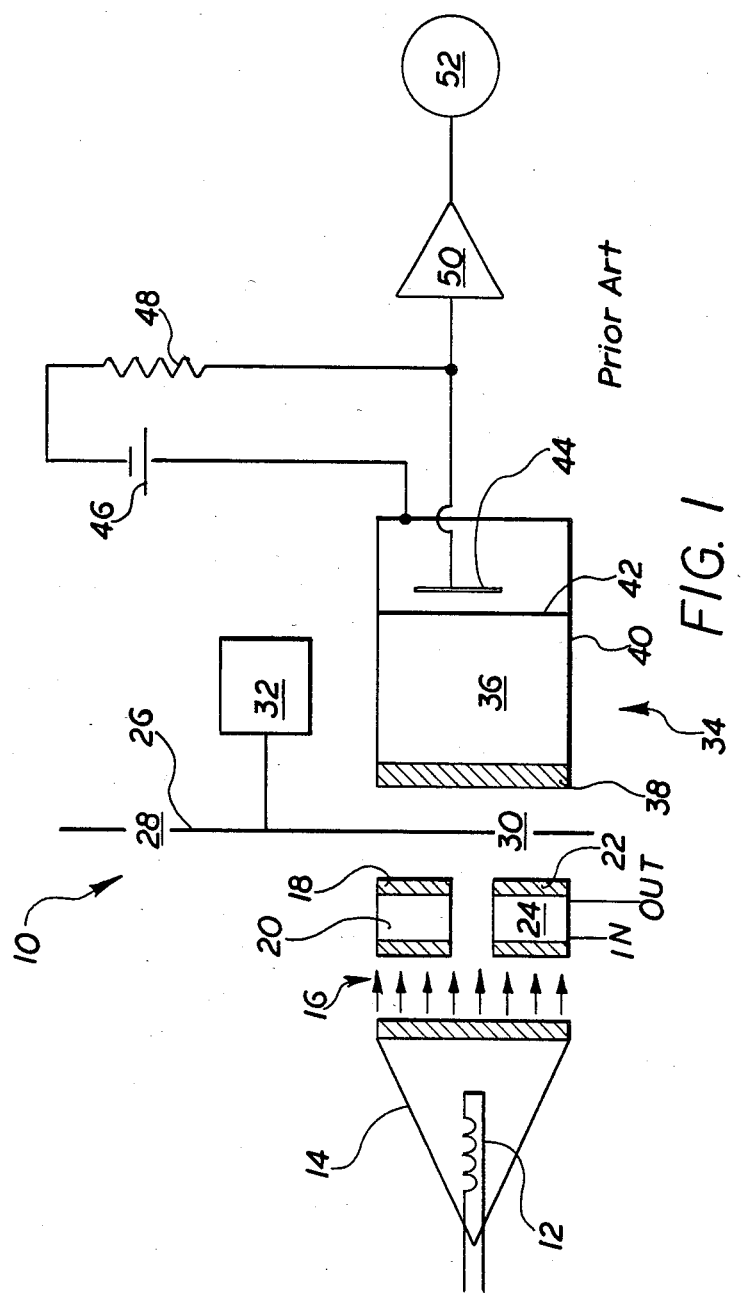
FIG. 1 is a schematic view of a prior art infrared fluid analyzer, included for purposes of explaining the present invention.

With reference to FIG. 1, there is schematically shown for purposes of understanding the present invention, an illustration of a conventional prior art infrared fluid analyzer 10. Prior art analyzer 10 includes a source of infrared radiation 12, a gathering and directing optical member 14 which produces a substantially collimated beam 16 of infrared radiation, a reference cell 18 containing selected fluid 20, a sample cell 22 into and out of which is passed the fluid 24 to be analyzed, a mechanical interruptor 26 having windows 28 and 30, a motor 32 for rotating interrupter 26 at a selected frequency, a pneumatic detector 34, amplifier 50 and a display meter 52. Pneumatic detector 34 includes a compartment 36 formed of a transparent front window 38, a housing 40 and a moveable diaphragm 42. A stator member 44 is positioned parallel and adjacent to diaphragm 42 and is electrically polarized with respect thereto by a source of electrical power 46 and a resistive element 48.

In operation, prior art analyzer 10 generally functions to detect the presence and relative amounts of a particular material within the fluid sample to be analyzed, through analysis of the absorption by the sample of characteristic wavelength lines within the infrared spectrum. In theory, source 12 emits a constant beam of infrared radiation into sample cell 22 and reference cell 18. The fluid sample 24 within the sample cell 22 absorbs characteristic wavelengths from the infrared spectrum which are not absorbed in the reference cell 18. Interruptor 26 rotates at a constant selected frequency such that windows 28 and 30 permit alternate pulses to pass therethrough from reference cell 18 and sample cell 22, respectively.

Pneumatic detector 34 receives the alternating pulses and detects the difference in infrared signal levels therebetween through the effect of the infrared signals on the pressure of the gas within compartment 36. The gas within compartment 36 is selected to be pressure responsive to the characteristic wavelengths absorbed in the sample cell 22, such that pressure changes occur in compartment 36 at the frequency at which interrupter 26 is operated. Such pressure changes are converted into a corresponding electrical signal by the capacitive element formed by diaphragm 42 and stator member 44, which are polarized by electrical source 46 and resistor 48. As diaphragm 42 moves in response to pressure changes in compartment 36, an electrical signal is produced corresponding to the changes in capacitance between diaphragm 42 and stator 44. The electrical signal is amplified by amplifier 50 and is conveniently displayed by meter 52.

Such a device, while satisfactory for many applications, is inherently limited in its sensitivity or signal to noise ratio by the presence of electrical source 46 and resistor 48 in the system. The noise reduction which would be realized by eliminating these contributors is defined by the following equation:

$$E^2 = 4RKT \cdot \Delta f$$

where
R=Resistance of resistor 48;
K=Boltzmann's Constant $(1.38 \times 10^{23}$ joules/°K.);
T=Degrees Kelvin;
$\Delta f$=Bandwidth of the electrical system in Hertz; and
E=RMS Noise Voltage Thus noise introduced by resistor 48 is directly related to the magnitude of resistance of resistor 48, which in systems of the type shown in FIG. 1 is commonly on the order of about 10,000 megohms. Of further significance is the relationship between the temperature of resistor 48 and noise introduced into the system; as temperature increases, noise increases. Thus, the noise in the system is subject to change during operation, thereby adversely affecting stability of the analyzer.

Figure 2:
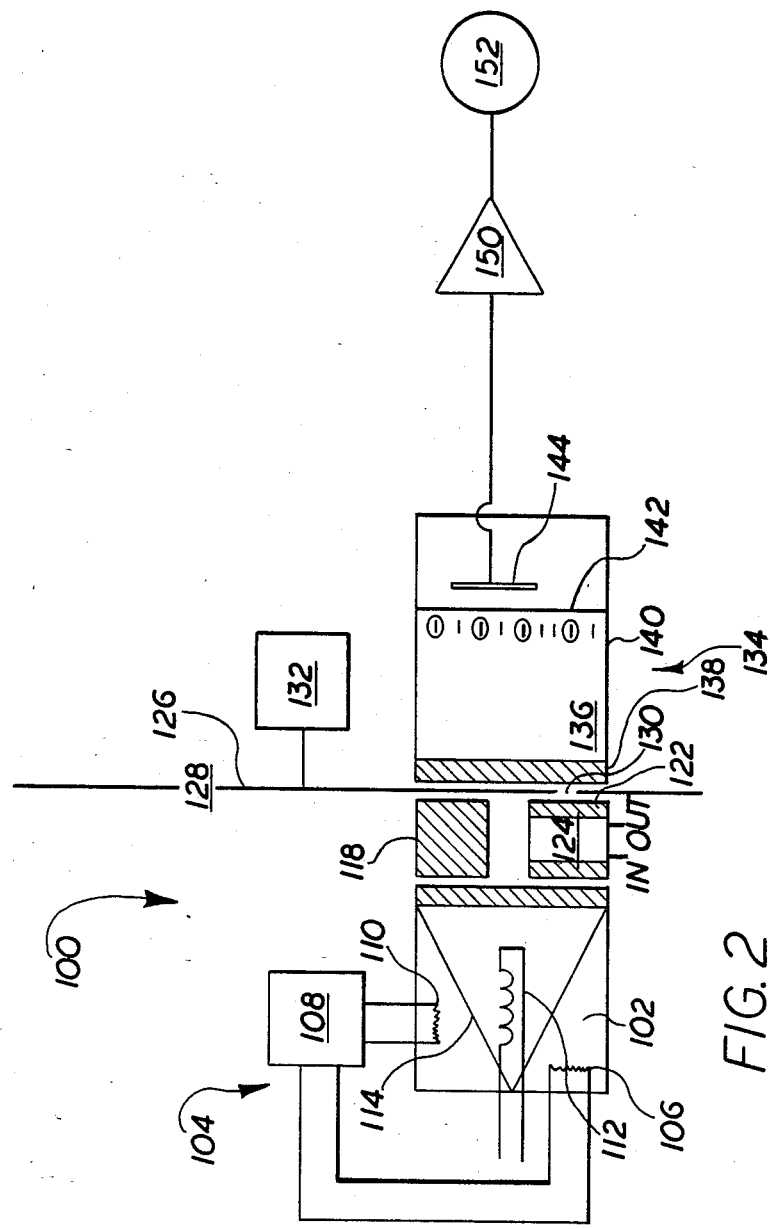
FIG. 2 is a schematic view of a double beam infrared fluid analyzer in accordance with the present invention.

With reference to FIG. 2, a novel infrared fluid analyzer 100 according to the present invention is schematically illustrated. Analyzer 100 operates in a substantially similar manner as analyzer 10, but incorporates a number of significant improvements thereof.

To be noted initially is the complete elimination of electrical source 46 and resistor 48 in polarizing diaphragm 142 and stator 144. This accomplishes the elimination of all of the electrical noise introduced into the system by such prior art elements and results in an analyzer 100 having a significantly improved signal to noise ratio, thereby permitting a greater sensitivity of analysis and a corresponding ability to identify more minute traces of a selected material within the fluids sample.

In the present invention, a facility for substantially noisefree polarization of diaphragm 142 and stator 144 is provided by forming at least a portion of diaphragm 142 and/or stator 144 of an electret material. An "electret" material is defined herein to mean a dielectric material which maintains a substantially constant and permanent stored electrostatic charge if utilized at temperatures below its Currie temperature. In one successful embodiment of the invention, diaphragm 142 is formed entirely of an electret material having an electrostatic charge thereon of $3.10^{-9}$ coul/cm$^2$ Commercially available electret microphones from the MURA Corp. of Westbury, N.Y. 11590 which are sold for applications in the audio industry have been determined to perform satisfactorily in the novel infrared fluid analyzer of the present invention. Preferably, a nontensioned electret microphone* is used where reduced temparature coefficients are desired such as a device is the Knowles Electronic, Inc. Model BT1759. Elk Grove Village, Ill.

*For more information, see A Subminiature Electret Condenser Microphone of New Design, *Journal of The Audio Engineering Society*, Vol. 22, p. 237 (1974) and A Subminiature Condenser Microphone, *The Hearing Dealer*, April (1973).

With continued reference to FIG. 2, it will be noted that analyzer 100 is significantly refined over analyzer 10 by the introduction of a temperature control chamber 102 about radiation source 112 and optical member 114. In cooperation with temperature control chamber 102 is provided a proportional temperature control system 104 consisting of a linear temperature sensor 106 connected to a proportional temperature controller 108 which controls the power of a resistance heating element 110 within chamber 102.

In operation, temperature control system 104 is intended to relatively quickly bring the temperature within chamber 102 up to a preselected steady state operating temperature and thereafter to maintain such operating temperature, independent of the period of use for several hours after radiation source 12 is initially activated. In the practice of the present invention each of these limitations of the prior art are substantially eliminated.

Preferably, resistance heating element 110 is activated concurrently with the initial activation of radiation source 112, in order to bring the system to the preselected operating temperature in a relatively short time period. Thereafter, temperature sensor 106 and controller 108 cooperate to maintain the operating temperature constant within chamber 102.

With further reference to FIG. 2, it will be appreciated that the sample cell 122 is positioned immediately adjacent to the exit end of chamber 102, as opposed to being spaced therefrom as shown in FIG. 1. This configuration is provided, in cooperation with temperature control system 104 discussed above, to assure that the temperature within sample cell 122 is maintained above the level at which condensation of gases would occur therein, e.g., above 100° C., during operation of analyzer 100. By maintaining close control over the temperature of chamber 102 and by positioning reference cell 118 immediately adjacent thereto, the present invention effectively also controls and maintains substantially constant the temperature of fluid sample 124, thereby eliminating any instabilities which might otherwise be introduced by temperature variations in the fluid sample.

With continued reference to FIG. 2, it is to be noted that reference cell 18 of FIG. 1 is replaced with an improved reference cell 118 in the practice of the present invention. Prior art reference cell 18 typically contained a gas within a hermetically sealed chamber, and served the purpose of an optically known constant through which collimated beam 16 would pass. In practice, however, reference cell 18 has been determined to be prone to leakage, which introduced an unknown into the optical system and adversely affected reliability of the instrument. In accordance with the present invention, reference cell 118 is formed from a selected solid material, thereby assuring that a true optical constant exists within the system. Preferably the solid material is selected to be nonabsorptive of the characteristic infrared wavelength lines that the fluid sample is expected to absorb. Materials such as calcium fluoride, barium fluoride, rock salt, quartz and others are expected to be useful in this type of application.

A presently preferred embodiment of the infrared analyzer of the present invention is shown in FIGS. 2a through 2d in which similar reference numerals refer to similar items shown on the schematic of FIG. 2.

In particular, a chamber 102' is provided with temperature control system 104' having resistance heating element 110'. A radiation source 112' provided a collimated beam for direction optical member 114' into the sample chamber. In the preferred embodiment reference cell 118' is a solid material (see FIGS. 2c and 2d) and sample cell 122' comprises a sealed window and gas inlet and outlet ports.

Interrupter 128' includes first and second opening 126' and 130' for permiting the passage of radiation from sample cell 122' and reference cell 118', respectively. Electrostatic microphone 142' is in pressure communciation with the gas in compartment 136'. Electrical amplification of the signals from microphone 142' is by means of amplifier circuit 150' which in turn is connected to meter (not shown) through wires 151'.

Figure 3:
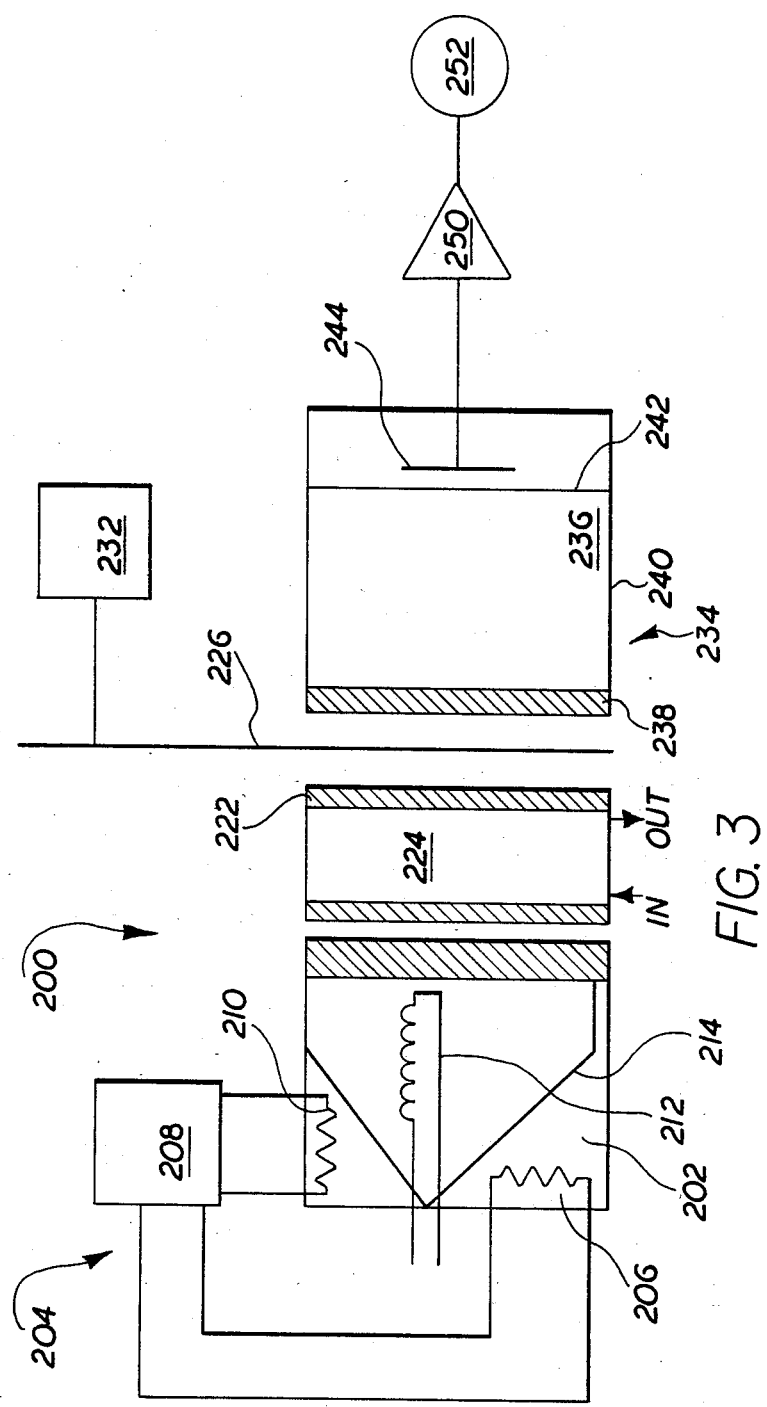
FIG. 3 is a schematic view of a single beam infrared fluid analyzer in accordance with the present invention.

With reference now to FIG. 3, there is shown a single beam infrared fluid analyzer 200 incorporating features of the present invention. Analyzer 200 includes many of the elements described above in the double beam analyzer 100, with the notable exception that a reference cell is not utilized in the operation of analyzer 200. As a result, pneumatic detector 234 receives intermittent pulses of infrared radiation from sample cell 222 which cause pressure changes within compartment 236. By appropriate electronic circuitry and calibration techniques known in the art, the electrical signal from pneumatic detector 234 is amplified and evaluated to determine the composition within the fluid sample 224. However, it will be appreciated that a single beam analyzer would be particularly sensitive to changes in the output from its radiation source which occurred as a result of temperature changes. Thus it is of added significance that analyzer 200 include temperature control chamber 202, temperature sensor 206, temperature controller 208 and resistance heating element 210 to maintain a constant (and quickly attainable) preselected operating temperature.

Figure 3A:
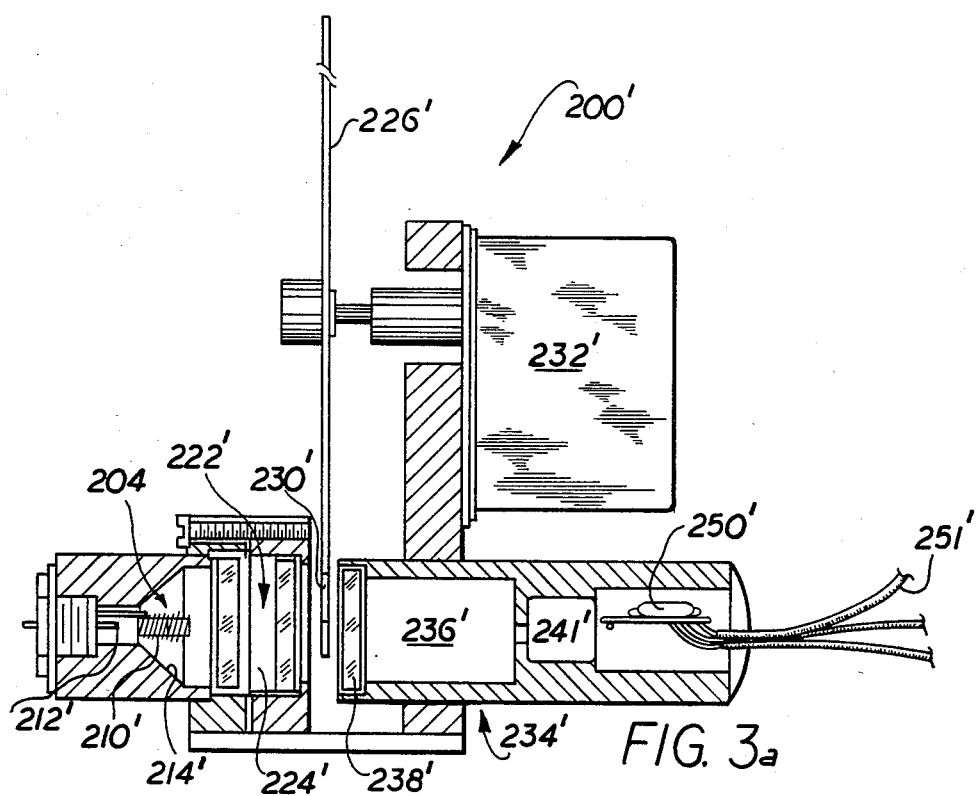
FIG. 3a and b is a presently preferred embodiment of the analyzer schematically shown in FIG. 3.
Figure 3B:
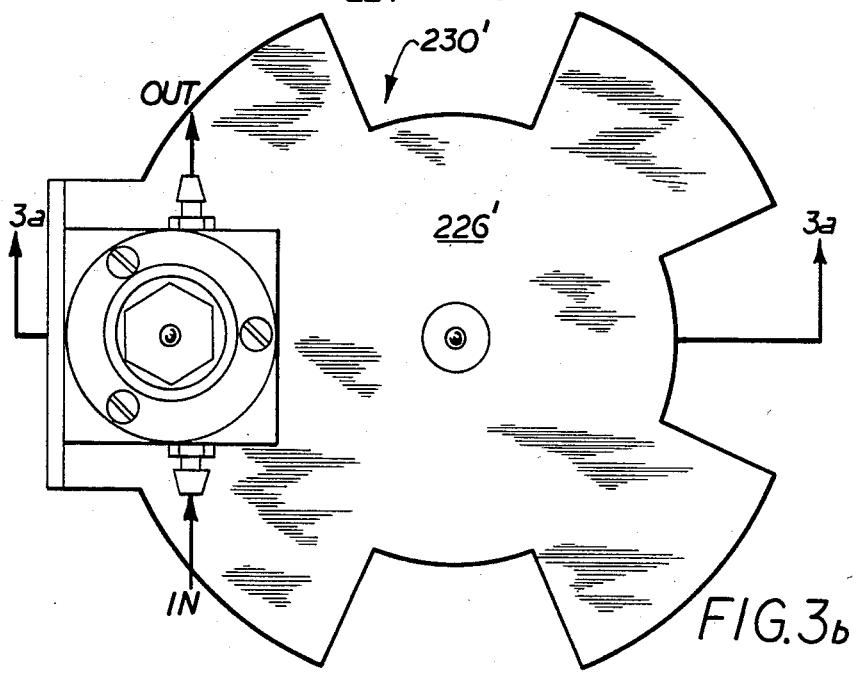

A presently preferred embodiment of the single beam analyzer of FIG. 3 is shown more particularly in FIGS. 3a and 3b wherein like reference numerals refer to like items in FIG. 3. Analyzer 200' is structurally similar to analyzer 100' shown in FIGS. 2a through 2d; however, interrupter 226' utilizes only one window 230' and the sampling cell 222' containing fluid sample 224' is a leakproof chamber without a reference cell.

Of course the present invention is not to be limited to the specific preferred embodiments described above, but rather by the claims which follow.

What is claimed is:

1. An infrared fluid analyzer comprising
   a. source means for producing a beam of infrared radiation;
   b. a sample cell in which fluid to be analyzed is contained, said sample being positioned in said beam of radiation;
   c. pneumatic detector means positioned to receive infrared radiation after passage through said sample cell, said detector consisting of
      i. a fluid chamber having a fluid responsive to changes in infrared radiation;
      ii. a diaphragm in communication with said fluid to move in response thereto;
      iii. stator means having one face spaced from and electrically connected to a second face on said diaphragm;
      iv. an electret material polarizer wherein the material forms at least a portion of the opposing faces of the diaphragm or stator means; and
   d. means for interrupting said beam from reaching said pneumatic detector.

2. An infrared fluid analyzer as set forth in claim 1, including a reference cell, said reference cell being positioned between said source and said detector and aligned with said means for interrupting such that alternately beams of infrared radiation from said sample cell and said reference cell pass to said detector and wherein said reference cell is formed of a solid material that is substantially nonabsorptive of the infrared radiation frequently absorbed by the fluid in said sample cell.

3. An infrared fluid analyzer as set forth in claim 2, wherein said reference cell is a nonabsorptive material selected from the group consisting of calcium fluoride, barium fluoride, rock salt and quartz.

4. An infrared fluid analyzer as set forth in claim 1, including a temperature control chamber for containing said source, said chamber having means for sensing temperature within said chamber, heating means, and means responsive to said sensing means for controlling said heating means to maintain a preselected operating temperature within said chamber.

5. An infrared fluid analyzer as set forth in claim 1, wherein said sample cell is positioned adjacent said source means to maintain said fluid contained therein at a temperature above its condensation point during operation of said analyzer.

6. The analyzer of claim 1 wherein the detector electrical elements comprise a non-tensioned electret microphone.

7. In an infrared fluid analyzer comprising a source of infrared radiation; a sample cell in which a fluid to be analyzed is contained; means for directing a beam of infrared radiation from said source through said sample cell; pneumatic detector means positioned for receiving said beam of infrared radiation after passage through said sample cell; and means for interrupting said beam of infrared radiation from reaching said pneumatic detector means from said sample cell; wherein said pneumatic detector means includes a fluid chamber containing a fluid which is pressure responsive to changes in said beam of infrared radiation incident upon said fluid chamber, a diaphragm member in communication with said fluid to move in response to pressure changes therein, stator means spaced from and electrically connected to said diaphragm member and means for electrically polarizing said diaphragm member and said stator means to produce a capacitance therebetween, the improvement comprising:

said polarizing means comprising an electret material forming at least a portion of said diaphragm member or said stator means, said electret material having a substantially constant electrostatic charge whereby movement of said diaphragm member produces an electrical signal corresponding to capacitance changes between said diaphragm member and said stator means and whereby electrical noise due to resistive elements is minimized in said infrared fluid analyzer.

8. The infrared fluid analyzer as set forth in claim 7, further comprising:

amplifier means for electrically amplifying said electrical signal; and display means for displaying the amplified electrical signal.

9. The infrared fluid analyzer as set forth in claim 8, further comprising:

a reference cell positioned between said source and said pneumatic detector means and cooperating with said directing means and said interrupting means such that said beam of infrared radiation passes to said pneumatic detector means alternately from said sample cell and said reference cell, wherein said reference cell is formed of a selected solid material which is substantially non-absorptive of infrared radiation of a frequency which is characteristically absorbed by said fluid to be analyzed.

10. The infrared fluid analyzer as set forth in claim 9, wherein said selected solid material is selected from the group consisting of calcium fluoride, barium fluoride, rock salt or quartz.

11. The infrared fluid analyzer as set forth in claim 7, further comprising:

a temperature control chamber for containing said infrared radiation source, said chamber including means for sensing temperature within said chamber, heating means, and means responsive to said sensing means for controlling said heating means to maintain a preselected operating temperature condition within said chamber to improve stability of said infrared fluid analyzer.

12. The infrared fluid analyzer as set forth in claim 11, wherein said heating means is actuated by said controlling means substantially concurrently with the initial actuation of said infrared radiation source to reach said preselected operating temperature condition in a shortened time period.

13. The infrared fluid analyzer as set forth in claim 11, wherein said sample cell is positioned adjacent said source of infrared energy in sufficiently close proxiity to maintain said fluid to be analyzed at a temperature above its condensation point during operation of said infrared fluid analyzer.

14. In an infrared fluid analyzer comprising a source of infrared radiation; a sample cell in which a fluid to be analyzed is contained, means for directing a beam of infrared radiation from said source through said sample cell and detector means for receiving said beam of infrared radiation after passage through said sample cell, the improvement comprising:

a temperature control chamber for containing said infrared radiation source, said chamber including means for sensing temperature within said chamber, heating means, and means responsive to said sensing means for controlling said heating means to maintain a preselected operating temperature condition within said chamber to improve stability of said infrared fluid analyzer.

15. The infrared fluid analyzer as set forth in claim 14, wherein said heating means is actuated by said controlling means substantially concurrently with the initial actuation of said source to reach said preselected operating temperature condition in a shortened time period.

16. An infrared fluid analyzer comprising
  a. source means for producing a beam of infrared radiation;
  b. a sample cell in which fluid to be analyzed is contained, said sample being positioned in said beam of radiation;
  c. pneumatic detector means positioned to receive infrared radiation after passage through said sample cell, said detector consisting of
    i. a fluid chamber having a fluid responsive to changes in infrared radiation;
    ii. a diaphragm in communication with said fluid to move in response thereto; and
    iii. stator means spaced from and electrically connected to said diaphragm, and
  d. means for interrupting said beam from reaching said pneumatic detector, and
  e. a reference cell positioned between said source and said detector and aligned with said means for interrupting such that alternately beams of infrared radiation from said sample cell and said reference cell pass to said detector and wherein said reference cell is formed of a solid material that is substantially nonabsorptive of the infrared radiation frequently absorbed by the fluid in said sample cell.

* * * * *